United States Patent [19]

Nakagawa et al.

[11] Patent Number: 5,558,841

[45] Date of Patent: Sep. 24, 1996

[54] WASHING/STERILIZING APPARATUS FOR AN ENDOSCOPE AND METHOD FOR WASHING/STERILIZING ITS WATER SUPPLYING SYSTEM

[75] Inventors: Mikihiko Nakagawa, Tokyo; Daisaku Negoro, Saitama-ken; Nobuyuki Nakanishi, Sagamihara; Akio Ogawa, Tokyo; Manabu Yajima, Tokyo; Toshihara Kinoshita, Tokyo, all of Japan

[73] Assignee: Olympus Optical Co., Ltd., Tokyo, Japan

[21] Appl. No.: 396,576

[22] Filed: Mar. 1, 1995

Related U.S. Application Data

[63] Continuation of Ser. No. 186,905, Jan. 26, 1994.

[30] Foreign Application Priority Data

| Apr. 26, 1993 | [JP] | Japan | 5-099332 |
| Aug. 17, 1993 | [JP] | Japan | 5-203318 |
| Nov. 30, 1993 | [JP] | Japan | 5-299697 |

[51] Int. Cl.$^6$ ............ G05D 7/06; A61L 2/18; A61L 2/24

[52] U.S. Cl. .......... 422/105; 422/300; 422/116; 134/104.1

[58] Field of Search .............. 422/292, 297, 422/300, 116, 28, 105, 62, 82.05; 68/12.02; 134/56 R, 58 R, 113, 104.1

[56] References Cited

U.S. PATENT DOCUMENTS

| 4,545,956 | 10/1985 | Ciszewski et al. | 422/28 |
| 4,925,495 | 5/1990 | Crisp et al. | 134/56 R |
| 5,083,447 | 1/1992 | Kiuchi et al. | 68/12.02 X |
| 5,256,371 | 10/1993 | Pippert | 422/116 X |
| 5,279,799 | 1/1994 | Moser | 422/292 |

FOREIGN PATENT DOCUMENTS

| 2251382 | 7/1992 | United Kingdom | 422/292 |

*Primary Examiner*—Robert Warden
*Assistant Examiner*—E. Leigh Dawson
*Attorney, Agent, or Firm*—Frishauf, Holtz, Goodman, Langer & Chick

[57] ABSTRACT

An apparatus comprises a washing water supply tank for supplying washing water to an endoscope placed on a washing and sterilizing bath and a sensor for determining whether or not the water supply tank needs washing or sterilizing. Further, in addition, the water supply tank is also washed and sterilized. A lamp and buzzer inform the user of a result of whether or not the water supply system needs washing and sterilizing.

14 Claims, 8 Drawing Sheets

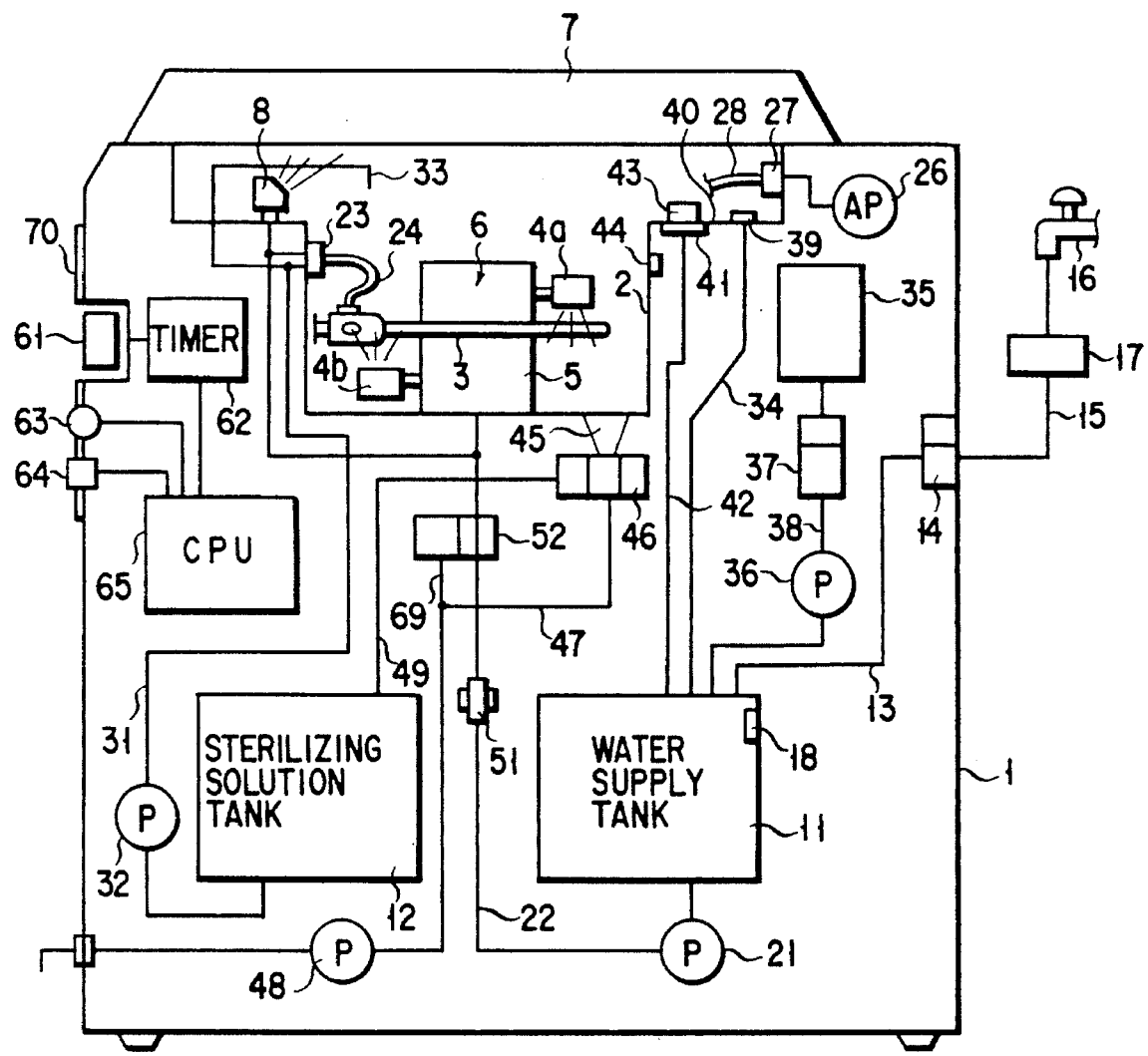
F I G. 1

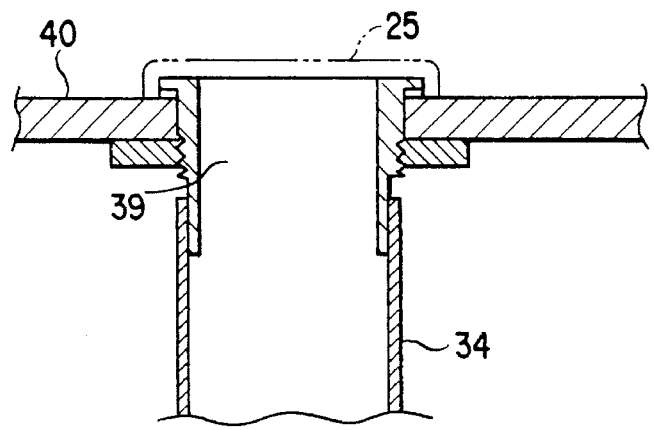
F I G. 4
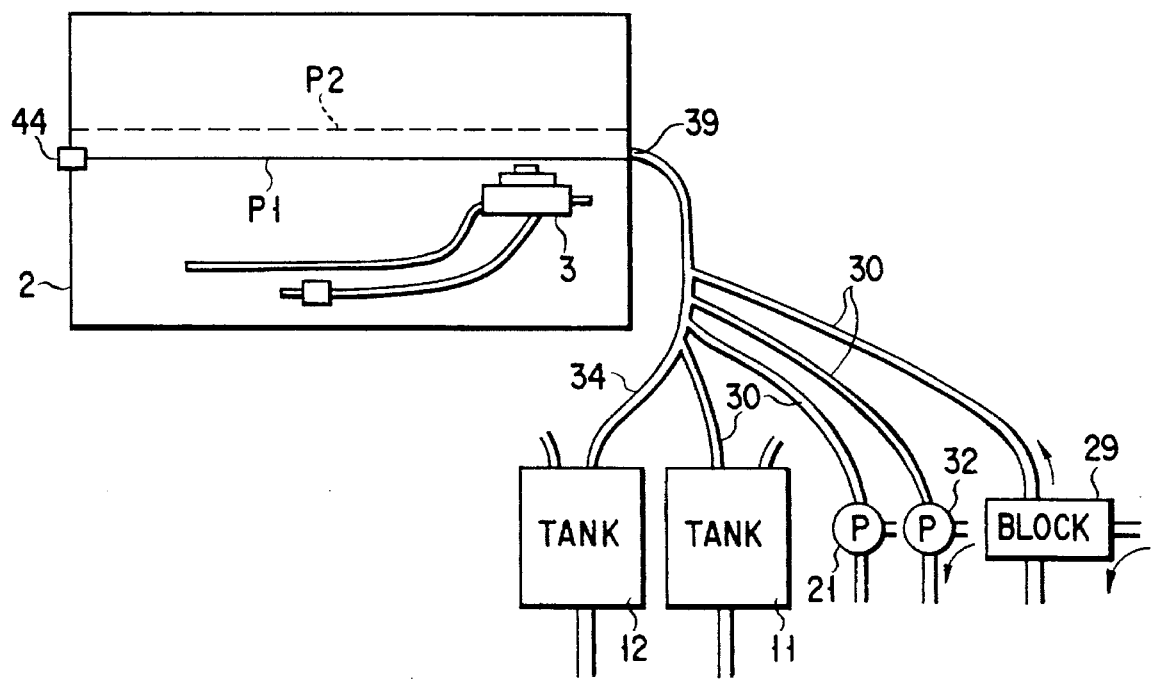
F I G. 5

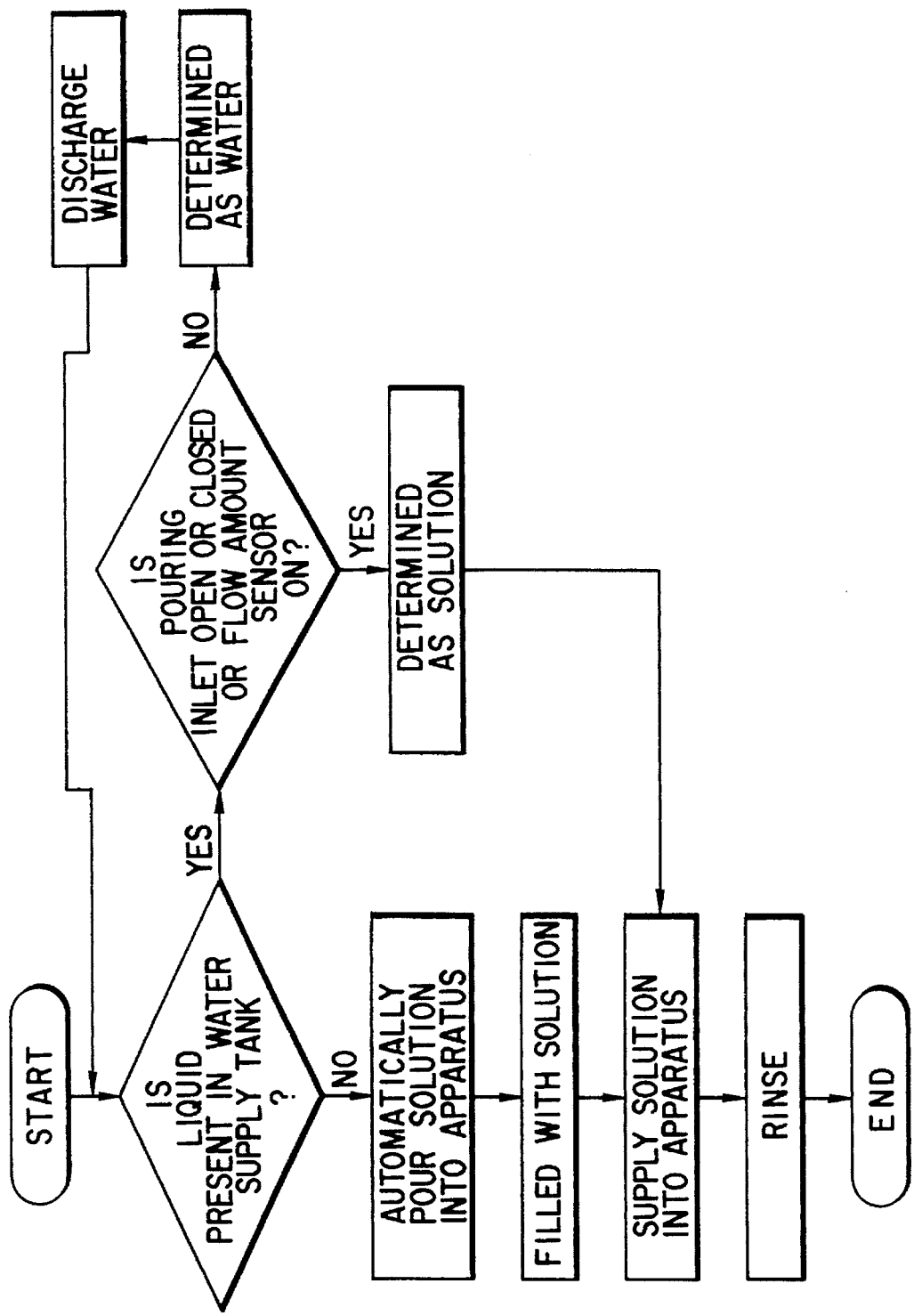
F I G. 10

5,558,841

WASHING/STERILIZING APPARATUS FOR AN ENDOSCOPE AND METHOD FOR WASHING/STERILIZING ITS WATER SUPPLYING SYSTEM

This application is a continuation, of application Ser. No. 08/186,905, filed Jan. 26, 1994.

BACKGROUND OF THE INVENTION

1. Field of the Invention

The present invention relates to a washing/sterilizing apparatus for an endoscope and a method for washing/sterilizing its water supplying system.

2. Description of the Related Art

In an endoscope it is necessary to wash/sterilize those component parts, etc., inserted, for example, into a living body after each use because a body fluid, a waste, etc., are involved. In the case where the endoscope is to be washed/sterilized by an endoscope washing/sterilizing apparatus after it has been used, the endoscope is set at a washing/sterilizing bath; then a waste deposited on the endoscope is removed by a jetted stream of water supplied through a washing nozzle of the washing/sterilizing bath where faucet running water is supplied through a water supply pipe; and finally the washed endoscope stays immersed in a sterilizing solution in the washing/sterilizing bath so as to sterilize it after the endoscope has been washed.

In this type of endoscope washing/sterilizing apparatus, after the endoscope has been washed/ sterilized, pools of water remain in the water supply tank and water supply pipe, thus providing possible breeding sites of various germs. After the endoscope has been washed/sterilized, it is necessary that the water left in the water tank and water supply pipe be forcibly drained by passing compressed air through the water supply tank and water supply pipe and, further, a sterilizing solution or alcohol be periodically fed through the water supply tank and water supply pipe so that the water supply tank and water supply pipe can be maintained sanitary.

However, the sterilizing operation, etc., of the water supply tank and water supply pipe are normally difficult and are left to the discretion of the operator and there is a possibility that such operation, etc., will be forgotten or not be properly done in a good timing.

SUMMARY OF THE INVENTION

It is accordingly the object of the present invention to provide an endoscope washing/sterilizing apparatus which can determine whether or not the apparatus interior through which washing water is flowed needs washing and/or sterilizing and can inform the user of that state so that the interior of the water supply system can be maintain clean and sanitary at all times and a method for washing/sterilizing the water supply system.

Further, the present invention provides an endoscope washing/sterilizing apparatus which can involve no extra cost for a sterilizing solution and no extra expenditure of effort on sterilization and can prevent multiplication of various germs, to a possible lowest extent, which might be produced in inner areas of a water supply system through which washing water is flowed and a method for washing/sterilizing the water supply system.

In order to achieve the object of the present invention there is provided an apparatus comprising:

means for placing the endoscope; a water supply system for supplying the washing water to the endoscope placed on the placing means; means for determining whether or not the water supply system needs washing and/or sterilizing; and means for, when the determining means determines that the water supply means needs washing and/or sterilizing, washing and/or sterilizing the water supply system. In addition, the present apparatus determines whether or not the interior of the water supply system needs washing and sterilizing and informs that result to the user so that the washing and/or sterilizing of the apparatus interior is performed in a proper timing and hence the water supply tank, water supply pipe, and so on can be maintained clean and sanitary at all times.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

FIG. 1 is a diagrammatic view showing an endoscope washing/sterilizing apparatus according to an embodiment of the present invention;

FIG. 4 is a cross-sectional view showing a sterilizing solution pouring inlet of the apparatus of FIG. 1;

FIG. 5 is a diagrammatic view showing an air vent pipe system in the apparatus shown in FIG. 1;

FIG. 10 is a flow chart showing another operation of CPU in the arrangement in FIG. 2;

DETAILED DESCRIPTION OF THE PREFERRED EMBODIMENTS

Figure 2:
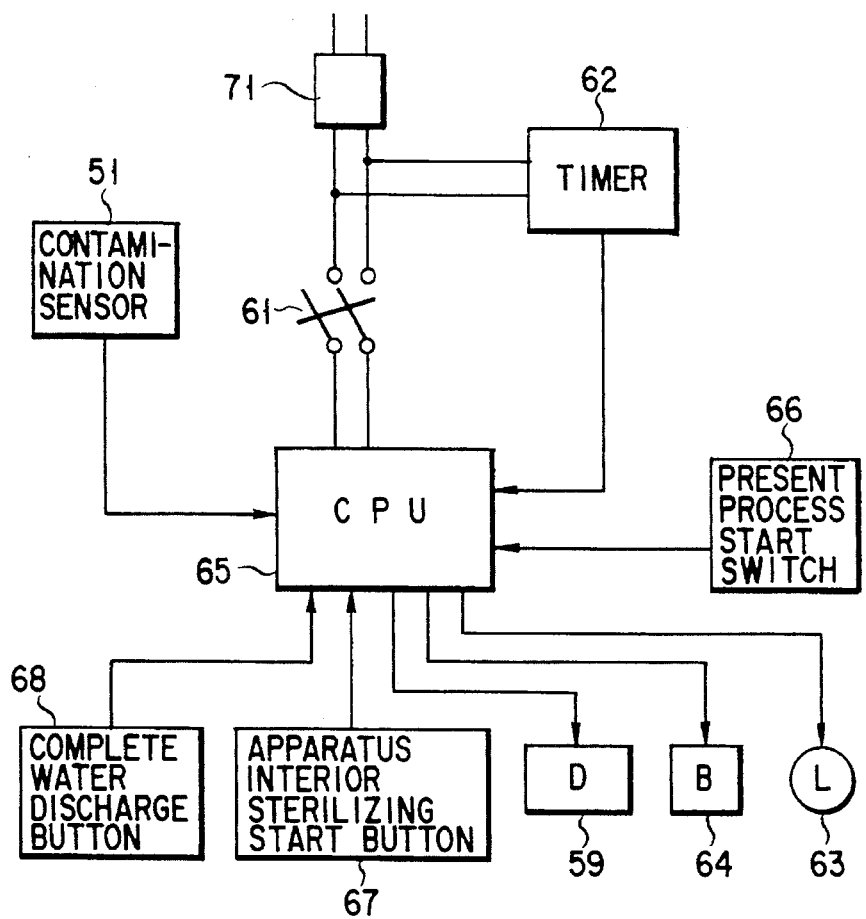
FIG. 2 is a view showing a control section of the apparatus of FIG. 1.

The embodiment of the present invention will be explained below with reference to the accompanying drawings.

FIG. 1 shows a diagrammatic arrangement of a washing/sterilizing apparatus for an endoscope. In FIG. 1, reference numeral 1 shows an apparatus body of the washing/sterilizing apparatus. A washing/ sterilizing bath 2 is provided at an upper zone of the apparatus body. An endoscope 3 to be washed/sterilized is placed in the washing/sterilizing bath 2. A washing nozzle device 6 has a rotating cylinder 5 including a nozzle 4a for applying a jetted stream of washing water from above to the endoscope 3 and a nozzle 4b for applying a jetted stream of washing water from below to the endoscope. The rotating cylinder is rotated.

An opening/closing type top cover 7 is provided relative to the washing/sterilizing bath 2 to cover the opening of the washing/sterilizing bath 2. A top cover washing nozzle 8 is provided at an upper side portion of the washing/sterilizing bath 2 to apply a jetted stream of washing water to the top cover 7.

A water supply tank 11 and sterilizing solution tank 12 are provided within the apparatus body 11. A pipe 13 for taking faucet running water is connected at one end to a water supply tank 11 and at the other end to an electromagnetic type water supply valve 14. The water supply valve 14 is connected by a pouring pipe 15 to a running water faucet 16. A water purifying device 17 is provided partway of the pouring pipe 15. The water purifying device 17 is comprised of, for example, an ultraviolet sterilizing device or a sterilizing filter.

By opening a running water faucet 16 and water supply valve 14, the water which is purified with the water purifying device 17 is fed, as replenishing water, into the water supply tank 11 of a water supply system through the water supply valve 14 and pipe 13.

A float switch 18 is provided in the water supply tank 11 to detect whether or not there is a predetermined amount of water in the water supply tank 11. With the float switch 18 OFF, that is, no water present in the water supply tank 11, the water supply valve 14 is automatically opened.

The water held in the water supply tank 11 of the water supply system is supplied, by a washing water supply pump 21, via a water supply pipe 22 in the water supply system to the upper and lower nozzles 4a and 4b on the washing nozzle device 6 and to a connector 23 leading to an endoscope channel. It is to be noted that the connector 23 is connected to the channel of the endoscope 3 via a supply tube 24.

A compressed air supply connector 27 is provided at the upper side wall of the washing/sterilizing bath 2 and communicates with an air pump 26 provided in the apparatus body 1. A pressure applying tube 28 is detachably connected to the compressed air supply connector 27 and also to an air passage connector provided at a light guide cable, not shown, of the endoscope 3.

A sterilizing solution supply pipe 31 is connected to a sterilizing solution tank 12 and a sterilizing solution pump 32 is provided partway of the sterilizing solution supply pipe 31. The sterilizing solution supply pipe 31 is connected to the connector 23 leading to the channel and to a sterilizing solution pouring inlet 33 opened to the washing/sterilizing bath 2. By the sterilizing solution pump 32, the sterilizing solution held in the sterilizing solution tank 12 is supplied through the sterilizing solution supply pipe 31 to the connector 23 and to the sterilizing solution pouring inlet 33.

A sterilizing solution tank 35 is provided within the apparatus body 1 to sterilize the interior of the apparatus. As the sterilizing solution held in the sterilizing solution tank 35, use can be made of an inexpensive one, such as an ampho soap, an invert soap and a chlorine-based sterilizing solution. The sterilizing solution tank-35 is connected to the water supply tank 11 through a sterilizing solution pipe 38 equipped partway with an electromagnetic valve 37 and sterilizing solution pump 36. When the interior of the apparatus is to be sterilized, the sterilizing solution held in the sterilizing solution tank 35 is supplied through the sterilizing solution pipe 38 into the water supply tank 11 by driving the sterilizing solution pump 36 with the electromagnetic valve 37 opened.

A sterilizing solution pouring inlet 41 is provided at a base 40 which is provided at an upper side area of the washing/sterilizing bath 2. The solution pouring inlet 41 is connected by a solution pouring pipe 42 to the upper area of the water supply tank 11. The pouring inlet 41 is normally closed by a cap 43. When the sterilizing solution is poured via the sterilizing solution pouring inlet 41 with the cap 43 removed, the sterilizing solution is poured into the water supply tank 11 directly through the pouring pipe 42. As the sterilizing solution poured from the sterilizing solution pouring inlet 41, use is made of a relatively powerful one, such as a glutaral-based sterilizing solution.

An air vent hole 39, together with the sterilizing solution pouring inlet 41, is provided at the base 40. The air vent hole 39 communicates with a top space of the water supply tank 11 past a communication pipe 34 having no lift on its way. The air vent hole 39 is used to vent air in the water supply tank 11 in the water supply system. The air vent hole 39 is opened at a height level near the base 40 as shown in FIG. 4. A cap 25 with a proper-diameter leak hole provided there may be of such a detachable mount type that it can be threadably inserted into the air vent hole 39. The air vent hole 39 is connected through the communication pipe 34 to the top of the water supply tank 11. The air vent hole 39 may be of such a type that, in order to achieve a smooth flow of a fluid through each associated part, the vent hole 39 communicates by a corresponding communication pipe 30 with a corresponding one of those areas necessary to vent air, such as the tanks 11 and 12, pumps 21, 32 and 36, blocks of the electromagnetic valves 14, 37, 46 and 52. FIG.5 shows a conceptual arrangement of one form of such an air vent system.

A liquid level sensor 44 is provided at the side wall of the washing/sterilizing bath 2 and adapted to detect the surface level of the washing water or a sterilizing solution held in the washing/sterilizing solution bath 2 and determine its amount.

A discharge outlet 45 is provided at the bottom section of the washing/sterilizing bath 2 and is connected through the switching type electromagnetic valve 46 to a discharge pipe 47. A discharge pump 48 is provided partway of the discharge pipe 47. When the discharge pump 48 is driven with the electromagnetic valve 46 switched to the discharge pipe 47 side and opened, the liquid held in the washing/sterilizing bath 2 can be discharged via the discharge pipe 47 to an outside.

A sterilizing solution recovery pipe 49 is connected at one end to the discharge outlet 45 through the electromagnetic valve 46 and at the other end to the sterilizing solution tank 12. When the electromagnetic valve 46 is opened by being switched to the sterilizing solution recovery pipe 49 side, the sterilizing solution held in the washing/sterilizing bath 2 can be recovered in the sterilizing solution tank 12.

At least one contamination sensor 51 is provided, partway of the water supply pipe 22, as one means for determining whether or not the interior of the water supply system needs sterilizing. The contamination sensor 51 constitutes one informing means, as will be set out below, which detects the transparence (turbidity) level, pH value, etc., of the washing water supplied from the water supply tank 11 to the washing/sterilizing bath 2 to detect the degree of soilage indirectly, for example, turns on a later-described warning lamp 63 or warning buzzer 64 depending upon the extent of soilage, and informs the user of the necessity to sterilize the interior of the water supply system through which the faucet running water is supplied, that is, to sterilize the interior of the apparatus.

Figure 3:
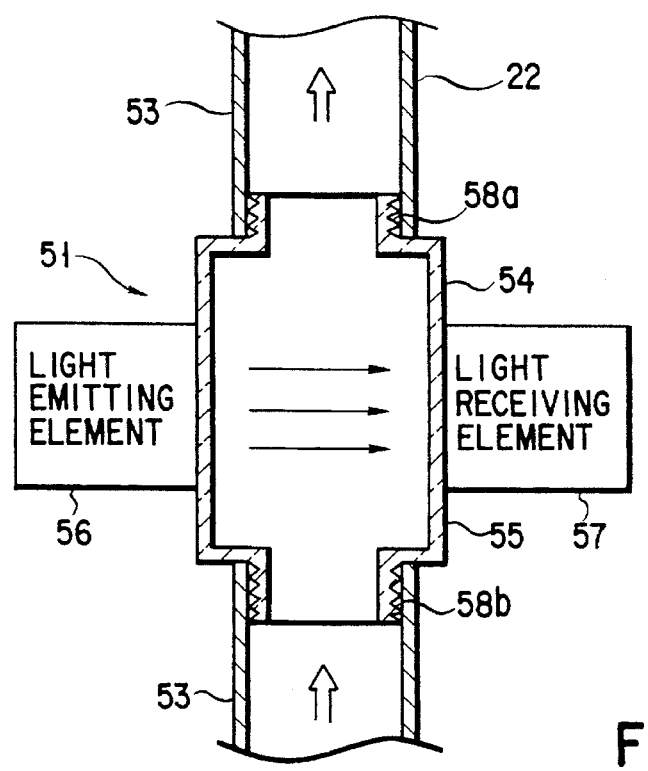
FIG. 3 is a cross-sectional view showing a portion of a contamination sensor of the apparatus of FIG. 1.

The contamination sensor 51 is constructed as shown, for example, in FIG. 3. That is, the sensor 51 comprises a checking type pipe passage 55 defined, partway of a pipe 53 forming the after supply pipe 22, by a pipe member 54 of a transparent material threadably inserted into the opposed pipe sections (53, 53) and a light emitting element 56 and light receiving element 57 arranged in opposed relation with the pipe passage 55 interposed. As the pipe member 54 use may be made of either a soft tube or a hard pipe member, such as transparent glass, in which case it is preferably inserted into the pipe member 53 in a threaded fashion. For this reason, the threaded end portions 58a, 58b of the pipe member 54 are so inserted into the pipe sections of the pipe 22 that their threading directions of the these threaded end portions 58a, 58b are opposite to each other. The contamination sensor 51 ensures more reliability if it is located as near to the washing nozzle device 6 as possible.

A drain pipe 69 is provided partway of the water supply pipe 22 via the switching valve 52. The switching valve 52 being switched to the drain pipe 69 side, the water supply pipe 22 is connected to the discharge pipe 47. By operating a later-described complete water discharge button 68 in this switched state, the water supply valve 14 is closed and the water supply pump 21 is operated so that the water held in the water supply tank 11 is completely discharged directly through the discharge pipe 47 (complete water discharge operation).

In FIGS. 1 and 2, reference numeral 61 shows a power supply switch and 62, a timer. The timer 62 constitutes a means for indirectly determining, by time control, whether or not the water supply system is to be washed and/or sterilized. For example, it is operated with the power supply switch 61 OFF and counts a time interval from that OFF state to an ON time and compares it with a set time (for example, eight hours after one night) and, if exceeding the latter time, turns on a warning lamp 63 and/or a warning buzzer 64 and informs the user of the necessity to sterilize the interior of the apparatus. Further, a display unit 59 is also provided to display characters, symbols, etc., on the necessity to sterilize the interior of the apparatus and to prompt the user to take a corresponding action.

FIG. 2 shows a general arrangement of a control section in the washing/sterilizing apparatus shown in FIG. 1. In FIG. 2, reference numeral 65 shows a CPU. When the power supply switch 61 is rendered from an OFF state to an ON state, CPU 65 reads a count value from the timer 62 and enables the warning lamp 63 to be turned ON, when the read-out count value exceeds a time period of one week, and the apparatus to be locked at that time so that, unless the interior of the apparatus is sterilized, the washing/sterilizing operation of the endoscope is inhibited.

In FIG. 2, reference numeral 66 shows a start switch for the present step of washing/sterilizing the endoscope; 67, a start button for sterilizing the interior of the apparatus; and 68, a complete water discharge button. An operation panel 70 is provided at an upper forward surface area of the apparatus body 1. The timer 62 is connected in parallel to a power supply (plug) 71 and to a power supply switch 61.

If, in this arrangement, a time period from the OFF state to the ON state of the power supply switch 61 exceeds, for example, eight hours after one night, the warning lamp 63 is turned ON, thus indicating to the user that the interiors of the water supply tank 11 and water supply pipe 22 need to be sterilized. The user recognizes that "lit" state of the warning lamp 63 and depresses the apparatus interior sterilizing start button 67 on the operation panel 70. By so doing, the sterilizing operation is performed on the interior of the water supply tank 11 and water supply pipe 22. It is, therefore, possible to make the interiors of the water supply tank 11 and water supply pipe 22 clean and sanitary.

In the case where the time period from the OFF state to the ON state of the power supply switch 61 exceeds, for example, a one-week period, the warning lamp 63 is lit and the washing/sterilizing operation is inhibited.

Although, in this embodiment, the operation of the timer 62 has been explained in connection with the OFF operation of the power supply switch 61, the informing means may be so constructed that, instead of being operated in interlock with the power supply switch 61, the timer 62 turns on the warning lamp 63 or warning buzzer 64 a given time period (for example, 24 hours, one week) after the apparatus has last been sterilized. Although, in this embodiment, both the warning lamp 63 and the warning buzzer 64 have been explained as being used as the informing means for informing the user of the necessity to sterilize the interior of the apparatus, that is, the interiors of the water supply tank 11 and water supply pipe 22, any one of the warning lamp 63 and warning buzzer 64 may be employed. Alternatively, one or both of the warning lamp 63 and warming buzzer 64 may be employed through a corresponding selective switching.

Now an explanation will be given below about the steps of washing/sterilizing the endoscope by the endoscope washing/sterilizing apparatus. The washing/ sterilizing method comprises the step of removing washing water in the apparatus, the step of detecting leakage in the endoscope, the step of washing the endoscope, the step of sterilizing the endoscope and the step of rinsing the endoscope, as will be set out below.

Remove Washing Water

In the case where the endoscope washing/sterilizing apparatus is to be used at a given start time of a day, any remaining water has initially been removed from the interior of the apparatus the previous night so as to remove any germs which might be multiplied at various parts of the water supply system including the water supply tank. This is started by a calendar-clock type timer 62 to allow CPU 65 to operate the means for removing any washing water remaining in the water supply system. When the start switch 66 is depressed, the control means of the endoscope washing/sterilizing apparatus is operated, thus discharging the washing water which remained the previous day in the water supply tank 11 and in the pipe of the water supply system, that is, removing the remaining water. Stated in another way, the water supply valve 14 and electromagnetic valve 46 are opened, while the water supply pump 21 and discharge pump 48 are operated for a predetermined period of time. By so doing, faucet running water (fresh water) is supplied via the replenishing pipe 13 into the water supply tank 11 and flowed from the water supply tank 11 via the water supply pipe 22 into the washing/sterilizing bath 2 and discharged to an outside through the discharge pipe 47. That is, any remaining water in the water supply system is emptied, noting that this is operationally similar to the washing step as will be set out below. In the operation, it may also be possible to switch the switching valve 52 to the drain pipe 69 side and discharge the water directly to the outside through the discharge pipe 47, not via the washing/sterilizing bath 2.

Then the water supply valve 14 is closed and the associated pump, etc., are continuously operated with the replenishing pipe 13 shut-off and the content of the water supply tank 11 is emptied for water discharge. This completely and effectively drains the washing water which might stay long in the water supply system.

Detect Leakage

The endoscope 3 is placed in the washing/sterilizing bath 2 and the forward end of the pressure applying tube 28 is connected by the air supply tube 28 to the light guide cable, not shown. The base end of the pressure applying tube 28 is connected to the compressed air supply hole 27. with a leakage detection operation button, not shown, depressed, the air pump 26 is operated and the compressed air is applied to the inside of the endoscope 3 via the pressure applying tube 28.

The discharge outlet 45 of the washing/sterilizing bath 2 is closed with the electromagnetic valve 46 switched. At the same time, the washing water supply pump 21 is operated. As a result, the faucet running water is supplied from the water supply tank 11 into the washing bath 2 to reach a predetermined water level after which the water supply pump 21 is stopped. Thus, the endoscope 3 stays immersed in the body of water.

Since, at this time, the inside of the endoscope 3 is placed under pressure, if any leak sites are present in the endoscope 3, air bubbles rise from these sites while being floated. The presence or absence of any leakage can be checked by the eye.

Wash the Endoscope

Initially, the water supply valve 14 is opened and faucet running water is supplied into the water supply tank 11. A water supply level at this time is restricted by the float switch 18 so that a predetermined amount of water is held in the water supply tank. With the start of washing, the washing water is supplied by the water supply pump 21 to the washing nozzle device 6 and to the connector 23 leading to the channel of the endoscope. In this way, the outer surface and channel of the endoscope are washed with the washing water. Further, the washing water is also fed to the top cover washing nozzle 8 and to the inner surface of the top cover 7. At this time, the discharge outlet 45 of the washing/sterilizing bath 2 is opened by the electromagnetic valve 46 and the spent water is sequentially discharged by the discharge pump 48 through the discharge pipe 47.

Sterilize the Endoscope

The sterilizing solution of the sterilizing solution tank 12 is fed by the sterilizing solution pump 32 into the washing/sterilizing bath 2 and into the channel of the endoscope 3. Since, at this time, the electromagnetic valve 46 closes the discharge outlet 45 of the washing/sterilizing bath 2, the sterilizing solution is held in the washing/sterilizing bath 2 to a required level at which time the solution level is detected so as to stop the supply of the sterilizing solution. In this embodiment, even after a final solution level $P_1$ has been detected as shown in FIG. 5, the sterilizing pump 32 continues to be operated under control of the timer. When the solution supplied reaches an initial pouring solution level $P_2$ somewhat higher than the final solution level $P_1$, the supply of the solution by the sterilizing solution pump 32 is stopped. The solution is overflowed by an amount corresponding to a difference between the initial pouring solution level $P_2$ and the final solution level $P_1$ and flowed from the air vent hole 39 through the communication pipe 34 into the water supply tank 11. With that sterilizing solution thus flowed it is possible to readily sterilize the interior of the air vent pipe system.

The level of the sterilizing solution in the washing/sterilizing bath 2 is finally brought to the final solution level $P_1$ whereby the endoscope is set in the sterilizing solution. After the supply of the solution has been stopped, the endoscope stays immersed in the sterilizing solution for a predetermined period of time so as to sterilize it. Thereafter, the electromagnetic valve 46 is switched to the sterilizing solution recovery pipe 49 side and the sterilizing solution in the washing/sterilizing bath 2 is freely run down into the sterilizing solution tank for recovery.

Rinse

This is a step of rinsing the endoscope 3 in the same way as the washing step above to remove the sterilizing solution which stays deposited on the endoscope 3. Thereafter, the endoscope 3 is taken out of the washing/sterilizing bath 2 and, as required, dewatered, dried and stored in a storage cabinet, etc.

Sterilize the Interior of the Apparatus

Figure 6:
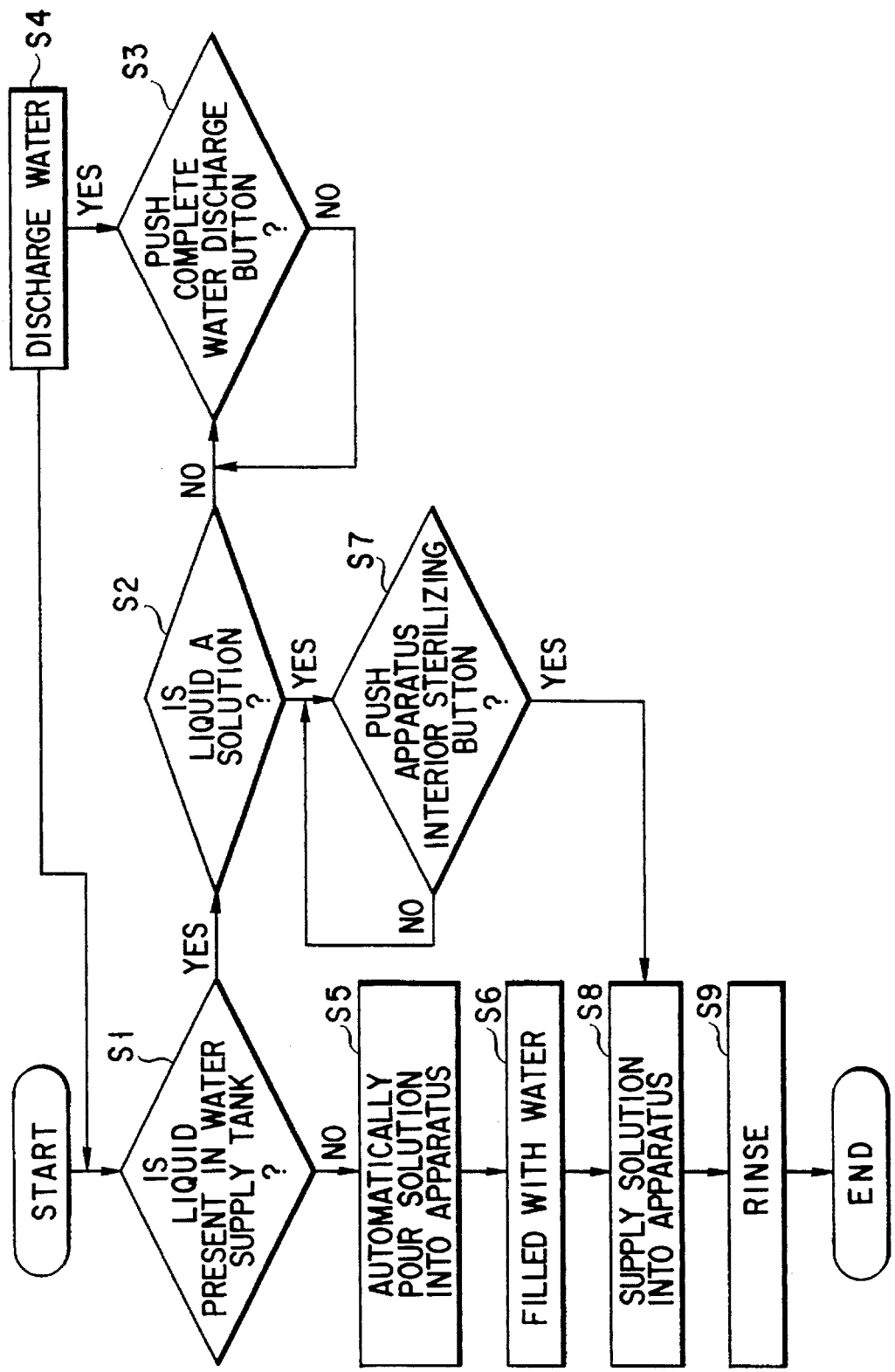
FIG. 6 is a flow chart showing another control operation of a CPU in an arrangement in FIG. 2.

An explanation will be given below about how to sterilize the interior of the apparatus based on the determination made by the warning lamp 63 or warning buzzer 64 so as for the interior of the water supply system to be sterilized or based on the alarm to that effect. FIG. 6 shows a flow chart of an operation process started by the depression of the sterilizing start button 67 so as to sterilize the interior of the apparatus.

That is, upon depression of the apparatus interior sterilizing start button 67, CPU 65 is responsive to a signal coming from the float switch 18 to determine whether or not there is any liquid remaining in the water supply tank 11 (step S1). If any liquid is present in the water supply tank 11, the sterilizing operation is not started on the interior of the apparatus and this fact is informed to the user by the lighting of the lamp, etc.

The user determines whether or not the liquid in the water supply tank 11 is a sterilizing solution (step S2). When the liquid in the water supply tank 11 is determined to be not a sterilizing solution, it is determined whether or not the complete water discharge button 68 is depressed (step S3). When the complete water discharge button 68 is depressed, control goes to step S4 and the liquid in the water supply tank 11 is completely discharged, and control is returned back to step S1.

In the case where the liquid in the water supply tank 11 is a sterilizing solution at step S2, control goes to step S7 and it is determined whether or not the sterilizing start button 67 is again depressed. When the sterilizing start button 67 is again depressed, control goes to step S8 to be later described.

In the case where it is determined that there is not any liquid in the water supply tank 11 (step S1), the interior of the apparatus is sterilized. When the sterilizing start button 67 is depressed, the electro-magnetic valve 37 is opened and pump 36 is operated at that time. The sterilizing solution held in the sterilizing solution tank 35 is poured in a predetermined quantity into the water supply tank 11 past the sterilizing solution pipe 38 so that the water supply tank 11 is filled with the sterilizing solution (steps S5 and S6).

When the water supply tank 11 is filled with the sterilizing solution, the sterilizing solution in the water supply tank 11 is supplied to the water supply pipe 22 in the water supply system (step S8).

In this way, the sterilizing of the apparatus interior is carried out and, when this sterilizing operation is completed, a rinse operation is done over and through the water supply tank 11 and water supply pipe 22 (step S9).

Such an arrangement prevents an unwanted liquid from being circulated through the apparatus and, further, the user can understand the situation involved, thus enabling the interior of the apparatus to be positively sterilized.

Figure 7:
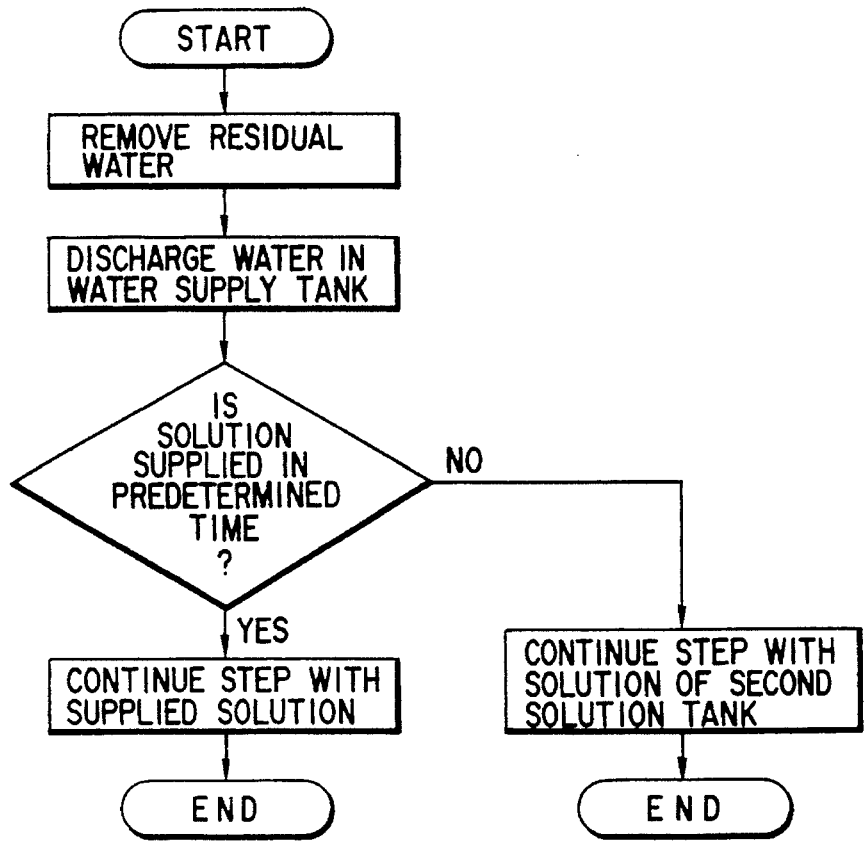
FIG. 7 is a flow chart showing another control operation of CPU in the arrangement in FIG. 2.

It may also be possible to sterilize the interior of the apparatus after the step of removing washing water from the above apparatus. After the step of removing the washing water from within the apparatus, a predetermined period of time is given for allowing the apparatus to receive a sterilizing solution. That is, as shown in a flow chart in FIG. 7, it is determined whether or not a sterilizing solution is introduced via the pouring inlet 41 into the water supply tank 11. If, for example, a specific sterilizing solution is introduced via the sterilizing solution pouring inlet 41 with the cap 43 removed, this sterilizing solution is employed at a subsequent apparatus interior sterilizing step. Unless, on the other hand, the supply of the sterilizing solution is not effected within the predetermined time period, a concentrated type sterilizing solution is automatically supplied from the sterilizing solution tank 35 into the water supply tank 11 with the electromagnetic valve 37 opened. At this time, the faucet running water is flowed into the water supply tank 11 with the water supply pump 14 opened to provide a diluted sterilizing solution as a practical solution. The diluted sterilizing solution is utilized at the step of sterilizing the interior of the apparatus.

At the subsequent step, the water supply pump 21 is operated, supplying the sterilizing solution in the water supply tank 11 to those associated pipes of the apparatus 11. At that time, the water supply valve 14 is closed. In order to secure an effective sterilizing period, that is, a time of contact of the sterilizing solution with the pipe wall, an intermittent operation is carried out, such as performing an operation in 10 seconds and then making a pause in 60 seconds, until the sterilizing solution in the water supply tank 11 is emptied. Thereafter, the water supply valve 14 is opened to supply the faucet running water and rinse the interior of the pipes of the water supply system, noting that this is the same operation as the washing step.

Here, as the solution of the sterilizing tank 35 for sterilizing the water supply system, use is made of an inexpensive one, such as an invert soap, ampho soap and chlorine-based sterilizing solution, etc. Unless any strong infection germs resistant to the sterilizing solution are present in the faucet running water, the interior of the apparatus is kept clean and sanitary if any sterilizing operation is performed, for example, every morning, at the starting time. If, on the other hand, it is necessary to employ any strong sterilizing solution, such as glutaral-based one, in a special case where the apparatus interior has already been heavily contaminated, any proper sterilizing solution is supplied from the sterilizing solution pouring inlet 41.

Although, as set out above, the air vent hole 39 is connected to the respective associated part to make the flow of the liquid smooth, it is also possible to sterilize the interior of the air vent pipe by flowing the sterilizing solution via the opening of the air vent pipe.

Figure 8:
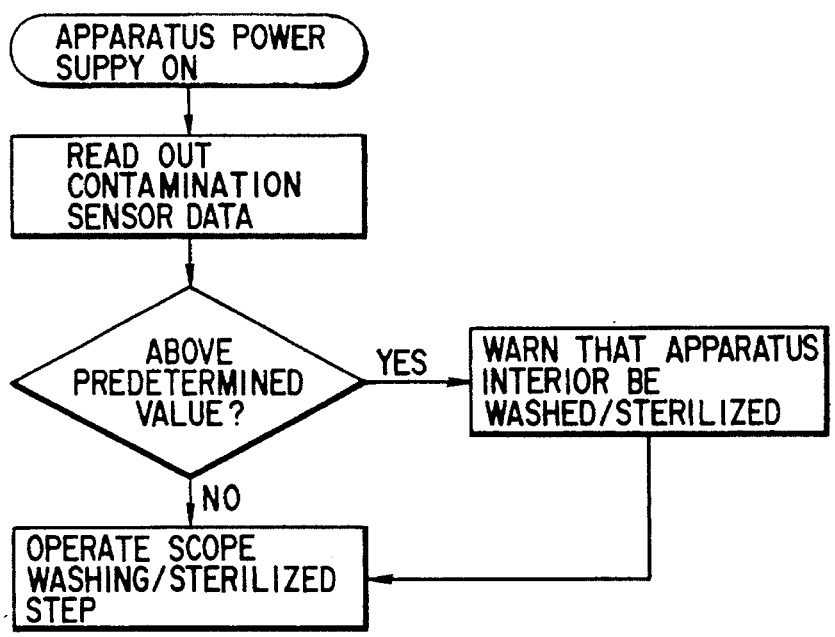
FIG. 8 is a flow chart showing another control apparatus shown in the arrangement in FIG. 2.

As shown in FIG. 8, on the other hand, the contamination sensor 51 detects the turbidity level and, when the turbidity level exceeds a predetermined level, it is determined that the water supply system is contaminated. At that time, the warning lamp 63 or warning buzzer 64 is turned ON, thus informing the user of the need to sterilize the interior of the apparatus. It is possible to take a proper action, by that warning, in a proper timing in those cases where, for example, the liquid is mixed with any heavily contaminated faucet water and any heavily contaminated endoscope 3 is to be washed. Thus, the user can perform the sterilizing operation on the interior of the apparatus.

Although the contamination sensor 51 is directly provided partway of the water supply pipe 22, any new detachable pipe for checking may be provided as a bypass passage relative to the water supply pipe or water supply tank 11, instead, in which case a similar contamination sensor 51 may be incorporated in the checking pipe. It may be possible to provide a contamination sensor in the washing/sterilizing bath 2 and detect the level of contamination in the washing water or a sterilizing solution in the washing/sterilizing solution bath 2. It may also be possible to not only detect the level of contamination of the washing water, as an object to be detected, but also detect the level of contamination of the sterilizing solution or the level of contamination of the water supply system based on the frequency with which the apparatus is used.

As the contamination sensor 51 use may be made of a sensor, etc., for optically detecting not only the level of transparency of the washing solution, etc., as set out above but also detecting the concentration level and pH value of the washing solution and sterilizing solution. The optical detecting system may detect any deposits, such as a scale or rust formed on the inner wall of the associated pipe and directly and indirectly detect an amount or level of such deposits on the inner wall of the associated pipes and tanks. By so doing it is possible to take any proper action.

Figure 9:
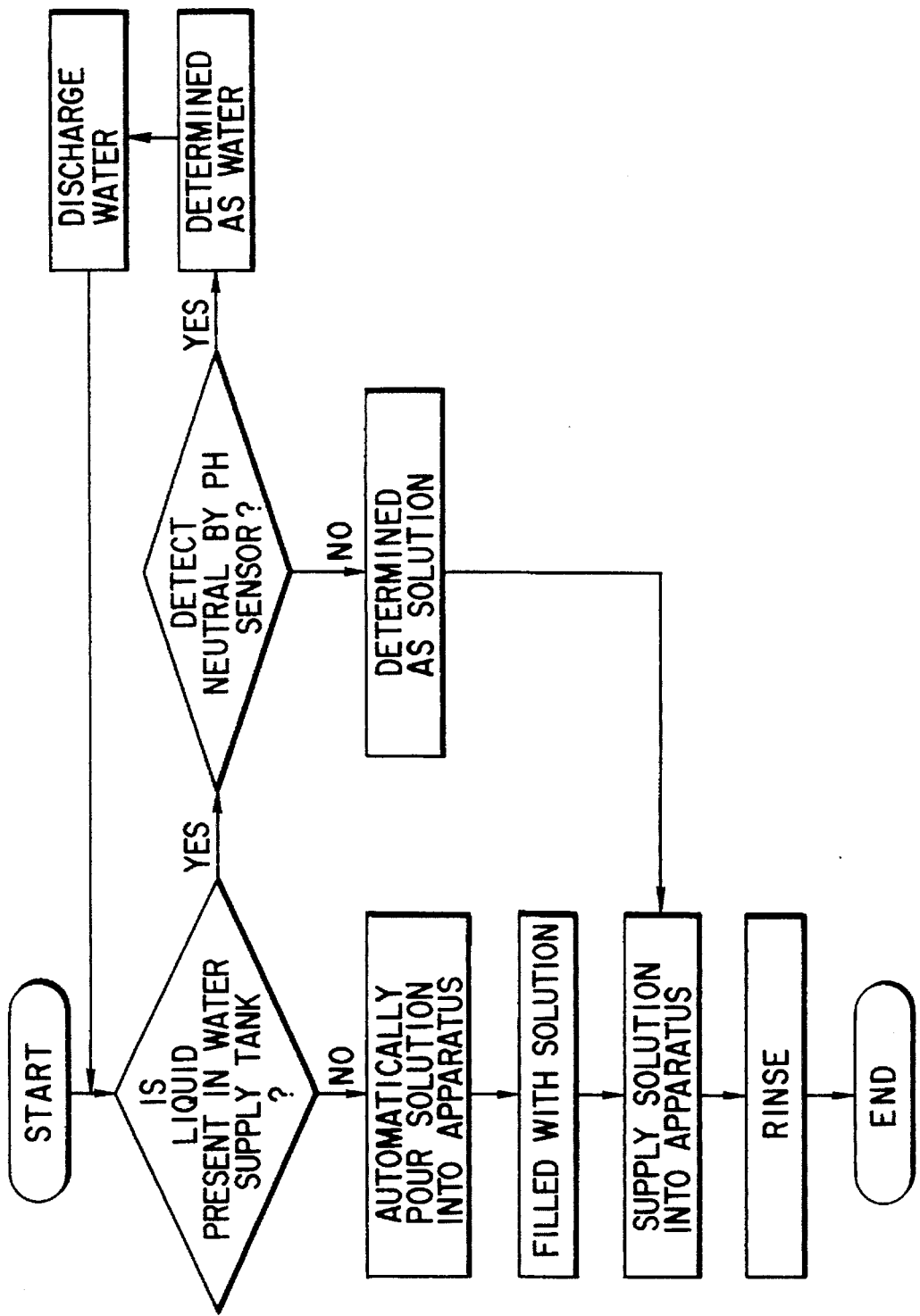
FIG. 9 is a flow chart showing another operation of CPU in the arrangement in FIG. 2.

In the case where it is determined whether or not the liquid in the water supply tank is a sterilizing solution, this determination may be done by providing a pH sensor on the water supply tank 11 and measuring the pH value of the liquid by the pH sensor, not the judgement of the user. FIG. 9 shows the procedure of this example. The same procedure as set out above can apply to this procedure except that the determination of whether or not the liquid in the water supply tank 11 be a sterilizing solution is made by the pH sensor.

The determination of whether or not the liquid in the water supply tank 11 is a sterilizing solution may be done by providing a means, such as a switch, for detecting the opening/closing of the pouring inlet 41 by detecting and attaching the cap 43 from and to the pouring inlet 41, or a flow amount sensor for detecting the flow of the sterilizing solution poured from the sterilizing solution pouring inlet 41 through the pouring pipe 42 into the water supply tank 11, and detecting whether or not the sterilizing solution is poured from the sterilizing solution pouring inlet 41 into the water supply tank 11. In this case, the determination of whether or not the solution in the water supply tank 11 is the sterilizing solution can be automatically effected by the opening/closing detecting means or flow amount sensor. In this case, the same operation as set out above is made except that an automatic determination is made as to whether or not the liquid in the water supply tank 11 is the sterilizing solution.

Although, in the respective case, the water supply system, being contaminated, is sterilized with a sterilizing solution, a washing operation may be performed on the water supply system to make its interior clean. As such a method, the washing operation for example is performed. At that time, the switching valve 52 provided partway of the water supply pipe 22 is switched to the drain pipe 69 side and the washing water may be discharged to an outside via the discharge pipe 47 by operating the water supply pump 21 through the operation of the complete discharge button 68. Further, by pouring the washing water via the sterilizing solution pouring inlet 41 instead of the sterilizing solution it may be possible to perform the same washing process as set out above.

Figure 11:
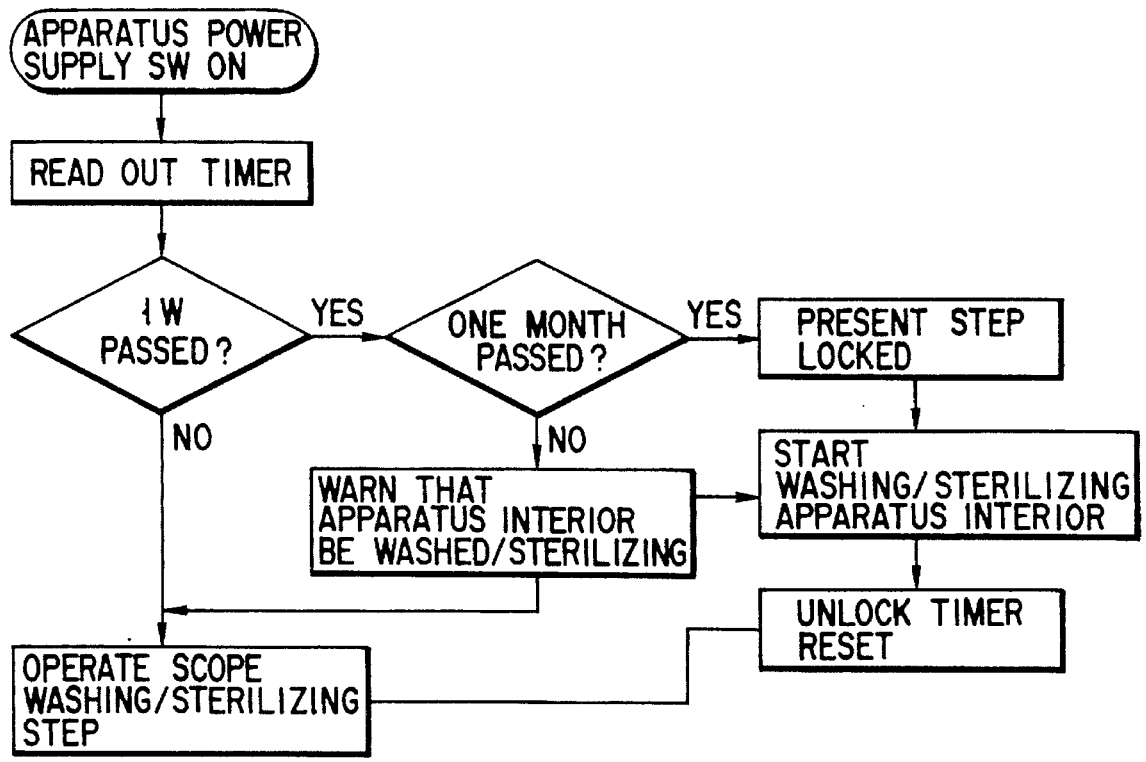
FIG. 11 is a flow chart showing another operation of CPU in the arrangement in FIG. 2.

The timer serving as a means for informing the user of the need to sterilize and/or wash the interior of the above-mentioned apparatus is of a calendar lock type and makes a count operation at an interval of, for example, one week. As shown in FIG. 11, the read operation of the timer 62 is started, after the power supply switch 61 has been turned ON, and an ordinary endoscope washing/sterilizing operation is done prior to the passage of one week.

After the passage of one week but before the passage of one month, a warning is give to the user to the effect that the apparatus interior be washed and/or sterilized. As required, the interior of the apparatus is sterilized and/or washed. The present process for washing and sterilizing the endoscope of the apparatus may be selectively employed.

After the passage of one month, the present process above is placed in a locked state. The apparatus is unlocked after the interior of the apparatus has been sterilized and/or washed. Further, the count of the timer 62 is reset.

If the timing with which the interior of the apparatus is sterilized and/or washed is controlled, it is possible to periodically sterilize and/or wash the interior of the apparatus at predetermined time intervals set by the manufacturer. According to this method, a cleaning operation can be carried out before the interior of the apparatus is heavily coated with a filthy matter. It is thus possible to obtain an advantage.

Figure 12:
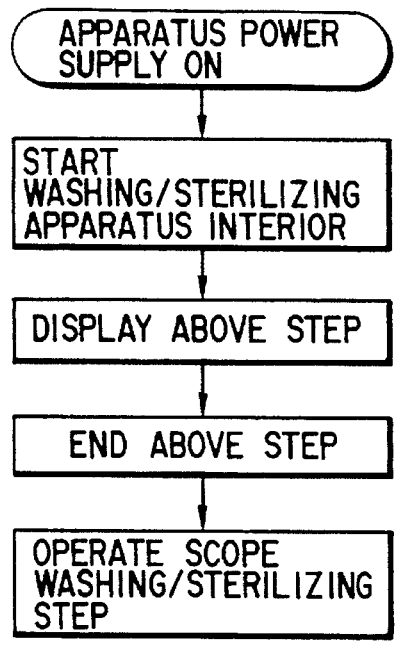
FIG. 12 is a flow chart showing another operation of CPU in the arrangement in FIG. 2.

If the timer 62 is of a calendar clock type, the interior of the apparatus is sterilized and/or washed when the calendar clock is turned ON, for example, when the power supply switch 61 is turned ON at a given start time every day or it may be possible to indicate to the user on a display to the effect that "the apparatus now being sterilized/washed" (See FIG. 12).

As the process in this case, the present process as set out above may be used and it may be possible to, with the endoscope 3 placed in the washing/sterilizing bath 2, perform an endoscope washing/sterilizing operation at least once. This is an emptying operation whereby pools of water still staying deposited on the pipes of the apparatus are drained therefrom to obtain an advantage. This process may be carried out each time the endoscope washing/sterilizing step is done. At this time, the switching valve 52 provided partway of the water supply pipe 22 as shown in FIG. 1 is switched to the discharge pipe 47 side. The washing water is force-discharged directly to an outside through the discharge pipe instead of flowing the washing water into the washing/sterilizing bath 2 with the endoscope 3 set there.

In the case where the water supply system is to be automatically washed and/or sterilized based on the result of determination by the means for determining whether or not the water supply system be washed and/or sterilized, those determining means are employed such as the calendar clock above, the count of the timer in interlock with the power supply switch, the count made by the timer started after the interior of the apparatus has been washed/sterilized, detection by each contamination sensor, and so on. In the case where the interior of the apparatus is to be automatically washed and sterilized, the start switch for the apparatus interior washing and/or sterilizing step is turned ON so long as the determining means determines that it is necessary to wash and/or sterilize the water supply system. During, or at the completion of this step, that state is informed to the user or it may be possible to provide a panel lock means for not accepting any other operations. When the endoscope washing/sterilizing step is to be performed, it is possible to secure the positive washing/sterilizing of the endoscope because the interior of the apparatus is kept clean and sanitary at all times without the user's intervention.

In the endoscope washing/sterilizing apparatus as set out above, the endoscope sterilizing bath 2 is filled with the sterilizing solution and the endoscope 3 stays immersed in the sterilizing solution. As the sterilizing solution use is usually made of a glutaral-based one. This solution is recovered in the sterilizing solution tank 12, without being thrown away, and repeatedly employed several times. The service life of the sterilizing solution stays effective until the sterilizing effect continues. This is so, depending upon the state in which the sterilizing solution is used. For example, the service life is influenced by a variation in time of a sterilizing solution used, the dilution with washing water of the sterilizing solution involved during circulation through the apparatus and the mixing of foreign matter into the sterilizing solution upon circulation through the apparatus. The sterilizing solution is often replaced with a new one when it expires the service life limit designated by the manufacture.

In order to replace the sterilizing solution with a new one, while the former retains its effective sterilizing effect, and obtain a positive sterilizing effect, the following action is desirably taken. For example, first and second count means are provided, the first count means counting the time interval and number of days starting from the last replacement of the sterilizing solution and the second count means counting the number of times the endoscope is sterilized under control of CPU 65. In order to replace the old sterilizing solution prior to the expiration of its effective life, these two count means are reset at the time the old sterilizing solution is disposed.

When a new sterilizing solution is to be poured into the apparatus, the data on the next replacing day and number of times the sterilizing operation is made are set on the apparatus so as to readily replace the sterilizing solution. The informing means gives a warning to the user when the service life limit is reached. A display unit for displaying the count number and warning characters is placed at a site upon which the user's attention is focused, thus giving a guide to the user so that the sterilizing solution can be replaced at a proper replacement time.

Further, the user sets the number of days and sterilizing number of times for replacement and, based on these set values, the respective counters inform the user of the time the sterilizing solution be replaced with a new one. Let it be supposed that the user sets seven days and 50 replacement times to the counters, assuming that a degradation resulting from a change with time of the solution per day corresponds to the degradation resulting from 5 dilutions involved. The warning is issued to the user when the solution is used a total of 75 times. The count is like this: 70 times at a second day, 65 times at a third day, 60 at a fourth day, 55 times at a fifth day, 50 times at a sixth day, 45 times at a seventh day, 40 times at an eighth day, . . . , 5 times at fifteen days and a warning is issued at a sixteenth day without making a count.

Given below is another example. That is, the initial concentration of a sterilizing solution to be used and concentration at a desired replacement time are set to the apparatus and the concentration of the solution is detected by the sensor as set out above. Since an amount of solution to be used is constant, the concentration level of the solution at a given time is calculated from the number of times the solution is used. The concentration level, exceeding a predetermined value, allows a warning to be issued to the user. Until the solution replacement is made, the starting operation of the washing/sterilizing process is inhibited.

In view of the service life limit of the solution, the replacement time is determined depending upon the situation under which the solution is used. The contamination of the water supply system is also increased under that situation. It is determined whether or not the water supply system is washed and/or sterilized in a way corresponding to the replacement time of the sterilizing solution. The replacement time is informed to the user so that the water supply system is washed/sterilized.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An apparatus for washing an endoscope with washing water and sterilizing the endoscope with sterilizing solution, comprising:

a bath for placing an endoscope therein;

a washing nozzle assembly for applying a jet of washing water to the endoscope placed in the bath;

a water tank;

a washing water passage for allowing only the washing water to flow when the endoscope placed in the bath is washed, a part of the washing water passage being connected between the water tank and the washing nozzle assembly;

a sterilizing solution passage for allowing only a sterilizing solution to flow when the endoscope placed in the bath is sterilized;

means for determining whether or not said part of the washing water passage needs sterilizing;

means for sterilizing said part of the washing water passage when the determining means determines that said part of the washing water passage needs sterilizing;

a tank for holding the sterilizing solution for sterilizing said part of the washing water passage;

a pouring inlet for pouring the Sterilizing solution into said part of the washing water passage so that the sterilizing solution is used for the means for sterilizing said part of the washing water passage;

means for detecting the pouring the sterilizing solution into said part of the washing water passage via the pouring inlet; and control means for, when the sterilizing solution pouring detecting means detects the pouring of the sterilizing solution by a selection of a user sterilizing said part of the washing water massage with the poured sterilizing solution and for, when the sterilizing solution pouring detecting means does not detect the pouring of the sterilizing solution by a selection of a user, sterilizing said part of the washing water massage with the sterilizing solution held in the tank.

2. The apparatus according to claim 1, wherein the determining means indirectly determines, under time control of a timer, whether or not said part of the washing water passage needs sterilizing.

3. The apparatus according to claim 2, wherein the timer contains a calendar, counts a time interval starting from a predetermined time in accordance with the calendar and determines whether or not said part of the washing water passage needs washing.

4. The apparatus according to claim 3, wherein the timer determines that said part of the washing water passage needs sterilizing by the calendar at a given start time of a day.

5. The apparatus according to claim 1, wherein the determining means determines, through detection, an extent to which the washing water in said part of the washing water passage is contaminated.

6. The apparatus according to claim 5, wherein the determining means has a transparent pipe through which the washing water in said part of the washing water passage passes and detects a contamination level on an inner wall of the transparent pipe.

7. The apparatus according to claim 1, wherein the determining means determines, through detection, a turbidity level of the washing water in said part of the washing water passage.

8. The apparatus according to claim 1, wherein the determining means has a timer for counting a time interval starting from the sterilizing of said part of the washing water passage.

9. The apparatus according to claim 1, further comprising means for restricting a start of an operation for sterilizing the endoscope when the determining means determines that said part of the washing water passage needs sterilizing.

10. The apparatus according to claim 1, further comprising informing means for, when said part of the washing water passage is in a state of needing sterilizing, informing said state to a user.

11. The apparatus according to claim 10, wherein the informing means comprises a buzzer.

12. The apparatus according to claim 10, wherein the informing means comprises a display lamp.

13. The apparatus according to claim 10, wherein the informing means comprises a character display unit.

14. The apparatus according to claim 1, wherein the means for sterilizing said part of the washing water passage includes removing means for, before flowing the sterilizing solution into said part of the washing water passage, removing residual washing water in said part of the washing water passage, wherein said part of the washing water passage is sterilized with the sterilizing solution after the washing water in said part of the washing water passage is removed by the removing means.

* * * * *